United States Patent
Yoon et al.

(10) Patent No.: US 8,965,068 B2
(45) Date of Patent: Feb. 24, 2015

(54) APPARATUS AND METHOD FOR DISCRIMINATING DISGUISED FACE

(71) Applicant: Electronics and Telecommunications Research Institute, Daejeon (KR)

(72) Inventors: Ho sub Yoon, Daejeon (KR); Chan Kyu Park, Daejeon (KR); Kye Kyung Kim, Daejeon (KR); Do-Hyung Kim, Daejeon (KR); Jae Hong Kim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 16 days.

(21) Appl. No.: 14/016,740

(22) Filed: Sep. 3, 2013

(65) Prior Publication Data

US 2014/0079295 A1    Mar. 20, 2014

(30) Foreign Application Priority Data

Sep. 18, 2012    (KR) ........................ 10-2012-0103375

(51) Int. Cl.
     *G06K 9/00*      (2006.01)
     *A61B 5/117*      (2006.01)

(52) U.S. Cl.
     CPC ................................... *A61B 5/1176* (2013.01)
     USPC ........................................ 382/118; 382/162

(58) Field of Classification Search
     USPC ................................................ 382/118, 162
     See application file for complete search history.

(56) References Cited

U.S. PATENT DOCUMENTS

| | | | |
|---|---|---|---|
| 7,076,088 B2 | 7/2006 | Pavlidis | |
| 7,561,791 B2 * | 7/2009 | Kakiuchi et al. | 396/155 |
| 8,295,557 B2 * | 10/2012 | Wang et al. | 382/118 |
| 2002/0044674 A1 * | 4/2002 | Pavlidis | 382/118 |
| 2004/0223629 A1 * | 11/2004 | Chang | 382/118 |
| 2007/0031032 A1 * | 2/2007 | Oh et al. | 382/167 |
| 2008/0019575 A1 * | 1/2008 | Scalise et al. | 382/118 |
| 2008/0192980 A1 * | 8/2008 | Park et al. | 382/103 |
| 2009/0074260 A1 * | 3/2009 | Kobayashi | 382/118 |
| 2009/0251278 A1 * | 10/2009 | Sheu | 340/5.2 |
| 2010/0158319 A1 * | 6/2010 | Jung et al. | 382/106 |
| 2010/0177939 A1 * | 7/2010 | Hamada | 382/118 |
| 2010/0177981 A1 * | 7/2010 | Wang et al. | 382/260 |
| 2011/0164792 A1 * | 7/2011 | Yoon et al. | 382/118 |
| 2011/0254942 A1 * | 10/2011 | Suzuki | 348/77 |
| 2012/0140091 A1 * | 6/2012 | Irmatov et al. | 348/222.1 |
| 2013/0163829 A1 * | 6/2013 | Kim et al. | 382/118 |

FOREIGN PATENT DOCUMENTS

| | | | |
|---|---|---|---|
| KR | 10-2006-0032247 A | 4/2006 |
| KR | 10-2010-0102449 A | 9/2010 |

* cited by examiner

*Primary Examiner* — John Strege

(57) ABSTRACT

An apparatus for discriminating a disguised face includes a face area detector configured to detect a face area in an input image provided from an external source. The apparatus includes a skin color modeling module configured to separate a skin color area from the face area and a disguised face discriminator configured to determine whether signals in the skin color area have a pulse component to discriminate whether a face in the input image is the disguised face.

18 Claims, 4 Drawing Sheets

APPARATUS AND METHOD FOR DISCRIMINATING DISGUISED FACE

RELATED APPLICATIONS

This application claims the benefit of Korean Patent Application No. 10-2012-0103375, filed on Sep. 18, 2012, which is hereby incorporated by reference as if fully set forth herein.

FIELD OF THE INVENTION

The present invention relates to a technique for disguised face discrimination, and more particularly, to an apparatus and method for discriminating a disguised face on the basis of whether a pulse component exists in a skin color area.

BACKGROUND OF THE INVENTION

A face image recognition technique is utilized in security systems, ATM (Automated Teller Machine) withdrawing systems, etc. A representative face image recognition system may be a face recognition system using a single camera. When a criminal or a person with a fraudulent intention inputs a disguised photo image through a camera with a purpose, the face recognition system has suffered from a difficulty in discriminating whether a face in the photo image is a disguised face or a genuine face.

In order to solve this problem, there has been proposed a method to discriminate a disguised face and a genuine face by detecting whether a face has an irregularity using a three-dimensional distance sensor or two cameras. However, the method using the three-dimensional distance sensor is relative expensive and has a disadvantage that it does not operate under natural light in an external environment. Meanwhile, the method using two cameras has a difficult to install the cameras in existing equipments and does not exhibit a satisfactory performance. Besides, the technique to discriminate whether a face is a photo image using the single camera uses a method to locate a border around a photo to verify the photo image. However, this technique has a limitation that does not verify a photo image which is cut in compliance with a face shape. In addition, it is difficult to discriminate a disguised face with a mask that is similar to and puts on a face or with a disguised silicon skip.

SUMMARY OF THE INVENTION

In view of the above, the present invention provides an apparatus and method for discriminating a disguised face, by extracting a skin color area from a face area and detecting whether the skin color area has a pulse component.

In accordance with an exemplary embodiment of the present invention, there is provided an apparatus for discriminating a disguised face, which includes: a face area detector configured to detect a face area in an input image provided from an external source; a skin color modeling module configured to separate a skin color area from the face area; and a disguised face discriminator configured to determine whether signals in the skin color area have a pulse component to discriminate whether a face in the input image is the disguised face.

In the embodiment, the skin color modeling module includes: a conversion unit configured to perform a coordinate system conversion on an image corresponding to the face area; a threshold setting unit configured to set threshold values using the image having the converted coordinate system; and a modeling unit configured to detect the skin color area using the threshold values.

In the embodiment, the modeling unit is configured to perform a binarization on the detected skin color area.

In the embodiment, the apparatus includes: a signal calculator configured to calculate a mean value of R, G, B signals in the binarized skin color area; and a buffer configured to store the mean value accumulatively; wherein the disguised face discriminator is configured to determine whether there exists the pulse component using the mean values stored in the buffer for a predetermined time period.

In the embodiment, the predetermined time period is 3 to 30 seconds.

In the embodiment, the apparatus includes: a signal processor configured to filter the mean values of the R, G, B signals stored accumulatively in the buffer to produce separated sources 1, 2, 3; wherein the disguised face discriminator is configured to analyze frequency properties of the separated sources 1, 2, 3 to evaluate periodicities and determine whether there exists the pulse component in accordance with the periodicities.

In the embodiment, the disguised face discriminator is configured to extract the frequency properties by applying FFT, MFCC (Mel-scale Frequency Cepstral Coefficient) and pitch to the separated sources 1, 2, 3 and train the extracted features using an SVM (Support Vector Machine) neural network training machine to determine the presence of the pulse component.

In the embodiment, the conversion unit is configured to convert an RGB image corresponding to the face area into HSV image or YIQ image.

In the embodiment, the RGB image corresponding to the face area is converted into HSV image, wherein the threshold setting unit is configured to calculate histograms with respect to H, S, V channels of the HSV image and set positions at which a total of pixel counts accumulated in left and right sides about peak positions of the respective histograms becomes a predetermined value to the threshold values for the respective H, S, V channels.

In accordance with another aspect of the exemplary embodiment of the present invention, there is a method for discriminating a disguised face, which includes: detecting a face area in an input image provided from an external source; detecting a skin color area from the face area; determining whether signals in the skin color area have a pulse component; and discriminating whether a face in the input image is the disguised face in accordance with the presence of the pulse component.

In the embodiment, the detecting a skin color area includes: performing a coordinate system conversion on an image corresponding to the face area; setting threshold values using the image having the converted coordinate system; and detecting the skin color area using the threshold values.

In the embodiment, the method includes: performing a binarization on the detected skin color area.

In the embodiment, the method includes: calculating a mean value of R, G, B signals in the binarized skin color area; and accumulatively storing the calculated mean value in a buffer;

In the embodiment, the determining whether signals in the skin color area have a pulse component includes:
determining whether there exists the pulse component using the mean values stored accumulatively in the buffer for a predetermined time period.

In the embodiment, the predetermined time period is 3 to 30 seconds.

In the embodiment, the method includes: filtering the mean values of the R, G, B signals stored accumulatively in the buffer to produce separated sources 1, 2, 3. wherein the determining whether signals in the skin color area have a pulse component includes: analyzing frequency properties of the separated sources 1, 2, 3 to evaluate periodicities and determine whether there exists the pulse component in accordance with the periodicity.

In the embodiment, the performing a coordinate system conversion includes: converting an RGB image corresponding to the face area into an HSV image or YIQ image from which brightness is separated.

In the embodiment, the RGB image corresponding to the face area is converted into an HSV image, wherein the setting threshold values includes: calculating histograms for HSV channels of the HSV image; and setting the threshold values in the histograms.

In the embodiment, the setting the threshold values in the histograms includes: setting positions at which a total of pixel counts accumulated in left and right sides about peak positions of the respective histograms becomes a predetermined value to the threshold values for the respective H, S, V channels.

In accordance with the embodiments of the present invention, the apparatus detects a pulse component on a basis of a signal change in the skin color area, thereby to improve reliability of the discrimination of the disguised face.

Further, the apparatus removes portions other than the skin color area in the face area through a color skin modeling to detect the pulse component, and, therefore, it is possible to detect pulse information significantly similar to real pulse information, and it is expected to speed up the detection of the disguised face.

BRIEF DESCRIPTION OF THE DRAWINGS

The above and other objects and features of the present invention will become apparent from the following description of the embodiments given in conjunction with the accompanying drawings, in which.

DETAILED DESCRIPTION OF THE EMBODIMENTS

The advantages and features of embodiments and methods of accomplishing the present invention will be clearly understood from the following described description of the embodiments taken in conjunction with the accompanying drawings. However, the present invention is not limited to those embodiments and may be implemented in various forms. It should be noted that the embodiments are provided to make a full disclosure and also to allow those skilled in the art to know the full scope of the present invention. Therefore, the present invention will be defined only by the scope of the appended claims.

In the following description, well-known functions or constitutions will not be described in detail if they would unnecessarily obscure the embodiments of the invention. Further, the terminologies to be described below are defined in consideration of functions in the invention and may vary depending on a user's or operator's intention or practice. Accordingly, the definition may be made on a basis of the content throughout the specification.

Hereinafter, an apparatus and method for discriminating a disguised face of the present invention will be described in detail with reference to the accompanying drawings.

Figure 1:
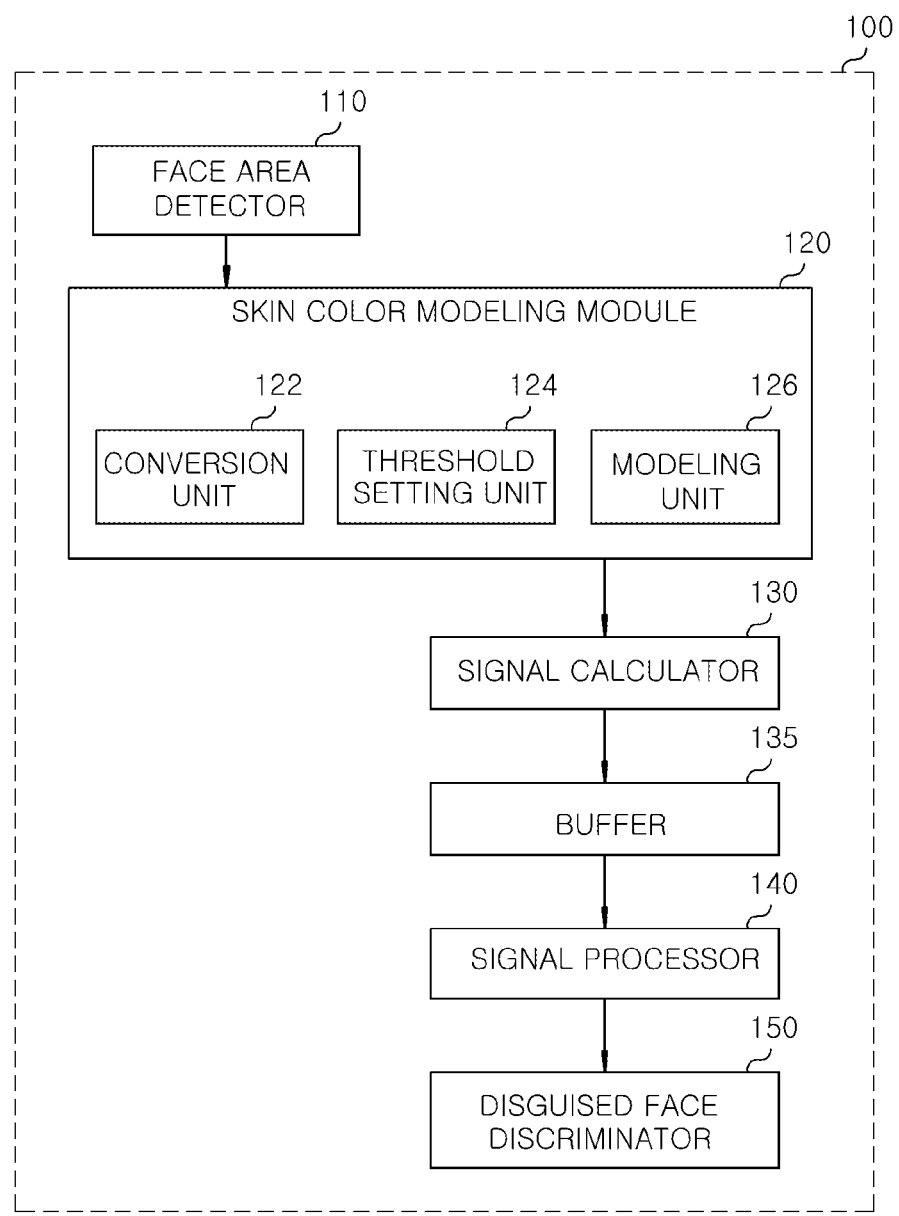
FIG. 1 is a block diagram of an apparatus for discriminating a disguised face in accordance with an embodiment of the present invention.

FIG. 1 is a block diagram of an apparatus for discriminating a disguised face in accordance with an embodiment of the present invention.

As illustrated in FIG. 1, a disguised face discriminating apparatus 100 in accordance with the embodiment includes a face area detector 110, a skin color modeling module 120, a signal calculator 130, a buffer 135, a signal processor 140, and a disguised face discriminator 150.

The face area detector 110 detects a face area in an input image provided from an external source. The schemes to detect the face area are well known to those skilled in the art, and therefore, a description thereof will not be made in detail. The face area includes different areas such as an eye, lip, naris, beard, and others, as well as a skin color area.

The skin color modeling module 120 separates the skin color area in the detected face area through a skin color modeling procedure. In other words, the skin color modeling module 120 performs a skin color modeling and binarization procedures to recognize a change in brightness of the skin color with the lapse of time.

The skin color modeling module 120 includes a conversion unit 122, a threshold setting unit 124 and a modeling unit 126.

The conversion unit 122 converts an input image which is significantly affected by lighting, e.g., RGB image into an image from which brightness information is separated. To be more specific, the conversion unit 122 converts the RGB image into an HSV (Hue Saturation Value) image or YIQ image to perform the modeling.

Hereinafter, the embodiment of the present invention will be described by way of example that the conversion is made from the RGB image into the HSV image will be discussed.

Figure 2A:
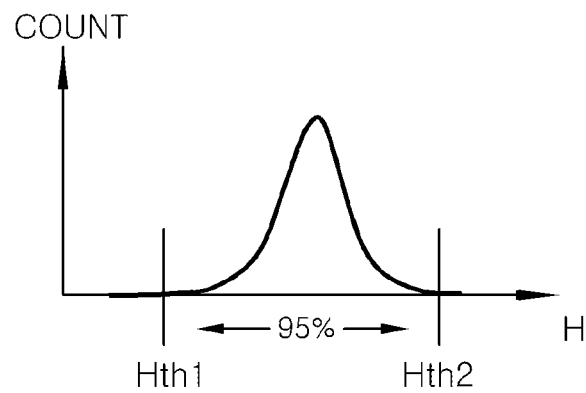
FIGS. 2A to 2C are diagrams illustrating the results of a threshold extraction procedure in accordance with an embodiment of the present invention.
Figure 2B:
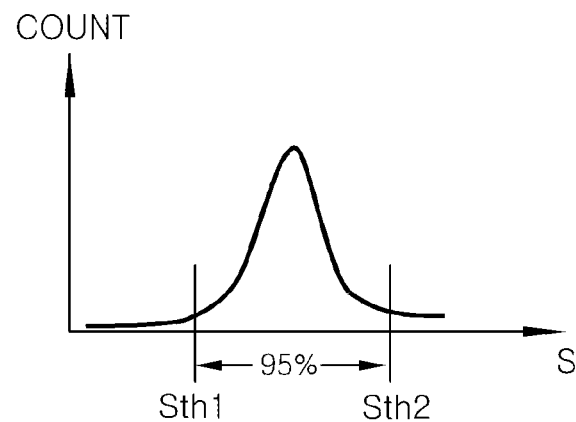
Figure 2C:
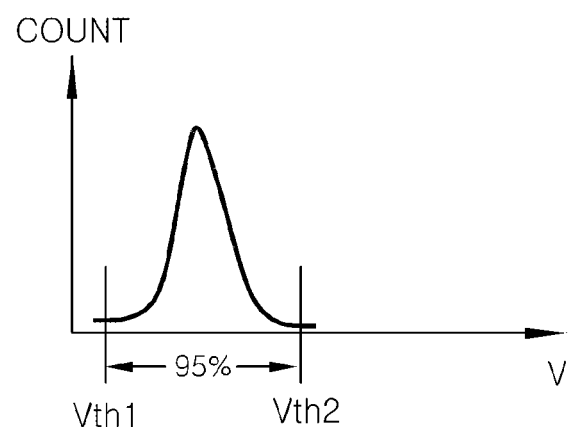

The threshold setting unit 124 calculates threshold values based on the converted HSV image. More specifically, the threshold setting unit 124 converts R, G, B channels into H, S, V channels with respect to the detected face area and generates histograms for the three channels, as illustrated in FIG. 2A, 2B and 2C. Further, the threshold setting unit 124 sets threshold values with respect to the H, S, V channels by searching positions at which a total of pixel counts accumulated in left and right sides about peak positions of the respective histograms becomes 95%, i.e., Hth1, Hth2 for H channel; Sth1, Sth2 for S channel; and Vth1, Vth2 for V channel. The extracted positions of the respective channels are set as the threshold values and are provided to the modeling unit 126.

Figure 3:
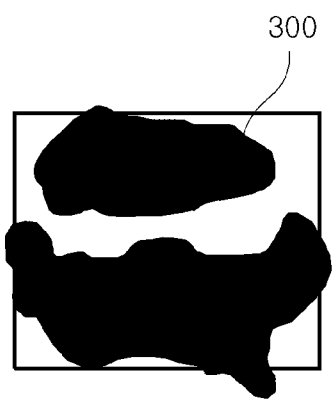
FIG. 3 is an exemplary diagram illustrating a result of a modeling procedure in accordance with an embodiment of the present invention.

The modeling unit 126 separates net skin color area except areas such as an eye, lip, naris, beard and the like having information other than the skin color, models the separated skin color area and binarizes the modeled area using the threshold values. For example, the modeling unit 126, as shown in FIG. 3, models only the skin color area and binarizes the modeled area 300.

The signal calculator 130 calculates a mean value of R, G, B signals in the binarized modeled area. The mean value is then stored in the buffer 135.

As described above, the face area detector 110, the skin color modeling module 120 and the signal calculator 130 detects a face area every frame, separates a skin color area from the face area, and extracts R, G, B signals to store them in the buffer 135.

The buffer 135 accumulatively stores the R, G, B signals and provides the accumulated R, G, B signals to the signal processor 140. For example, the R, G, B signals may be accumulated for 3 to 30 seconds, and the accumulated R, G, B signals may then be provided to the signal processor 140.

The signal processor 140 performs an adaptive filtering on the R, G, B signals to create separated sources, which will be used to determine whether they are a pulse signal. More specifically, the signal processor 140 filters an R signal to produce a separated source 1; filters a G signal to produce a separated source 2; and filters a B signal to produce a separated source 3.

The signal processor 140 may be, for example, ICA (Independent Component Analysis) or its applications, but is not limited thereto.

Figure 4:
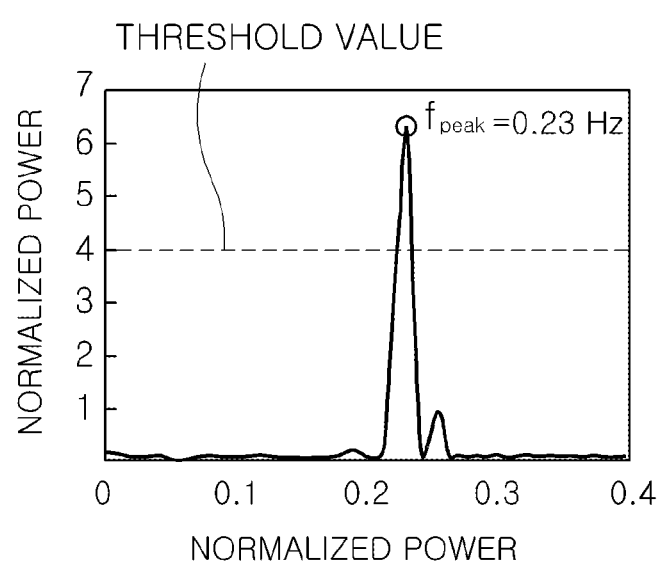
FIG. 4 is a diagram illustrating a pulse component detection procedure performed in the disguised face discriminating apparatus in accordance with an embodiment of the present invention.

The disguised face discriminator 150 analyzes a frequency properties in the separated sources 1, 2, 3 to evaluate periodicities and determines whether the separated sources 1, 2, 3 are a pulse signal in accordance with the periodicities. A method to determine whether the separated sources 1, 2, 3 has a pulse component is accomplished by calculating normalized Lomb Periodgrams to the frequency of the separated sources 1, 2, 3, illustrated in FIG. 4, comparing a power at frequency $f_{peak}$ at a point having maximum power_ and a predetermined threshold value.

The disguised face discriminator 150 discriminates whether a face in the face area is a disguised face or a genuine face in accordance with the presence of the pulse component.

While the embodiment of the present invention has been described by way of example that the determination whether there exists the pulse component is made using the method of normalized Lomb periodogram, it may be accomplished another way of extracting feature information using FFT, MFCC (Mel-scale Frequency Cepstral Coefficient), pitch or the like from the separated sources 1, 2, 3, which are obtained by the signal processor 140, and training the extracted feature information using a training machine such as a SVM (Support Vector Machine) neural network to determine whether there is present the pulse signal.

The operation of the disguised face discriminating apparatus having such configuration as set forth above will be discussed with reference to FIG. 5.

Figure 5:
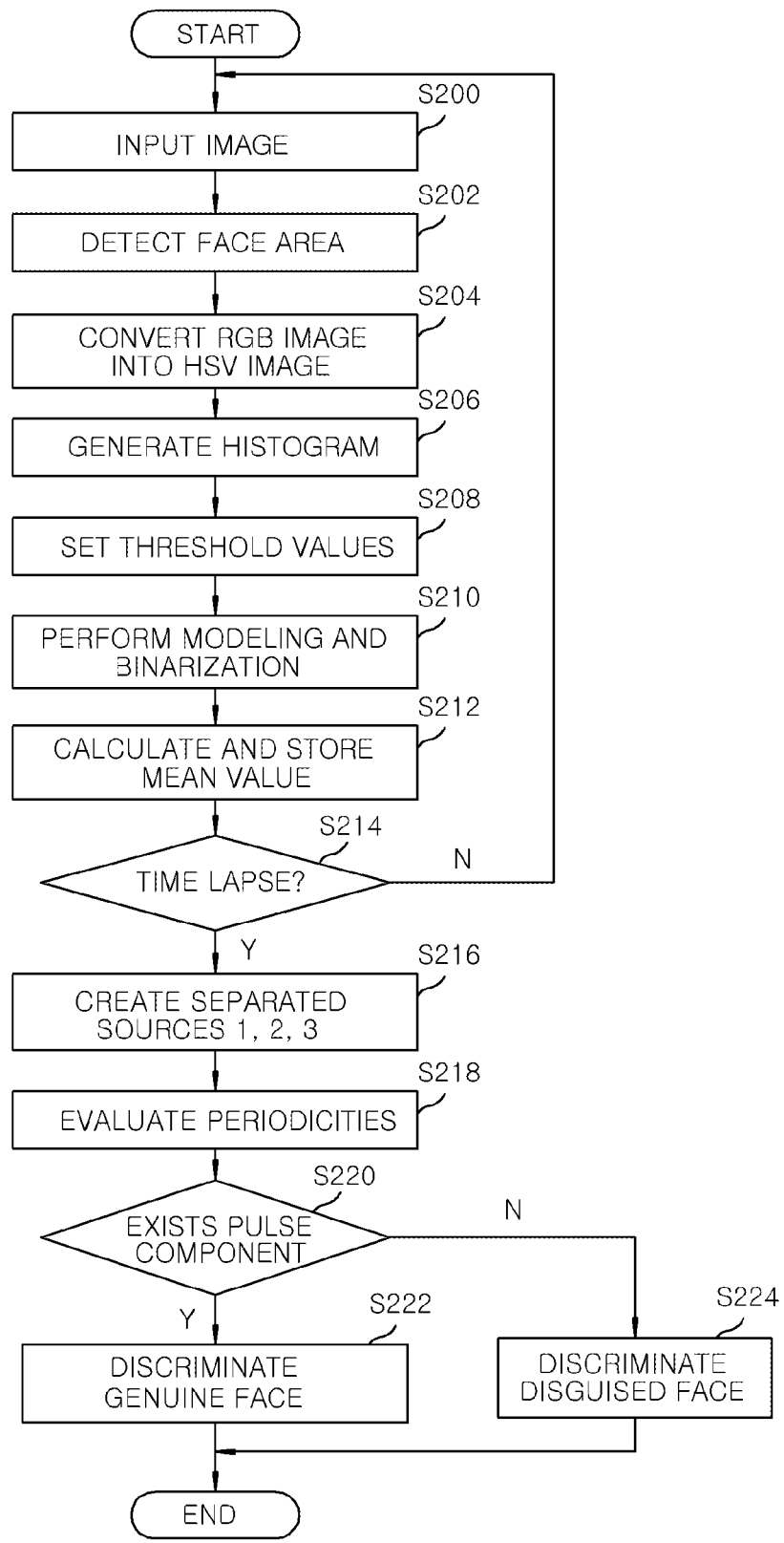
FIG. 5 is a flow chart illustrating a method for discriminating a disguised face in accordance with an embodiment of the present invention.

FIG. 5 is a flow chart illustrating a method for discriminating whether a face in the input image is a disguised face in accordance with an embodiment of the present invention.

As illustrated in FIG. 5, the method begins with operation s200 where an image captured by a camera or the like is input or an image is input from an external source. The face area detector 110 detects a face area in the input image, in operation s202. An RGB image corresponding to the detected face area is then provided to the skin color modeling module 120.

The skin color modeling module 120 converts a coordinate system of the RGB image of the face area through the use of the conversion unit 122. For example, the RGB image is converted into an HSV image, in operation s204.

Thereafter, the threshold setting unit 124 generates histograms of three channels, i.e., H, S, V channels through the skin color modeling procedure, in operation s206.

The threshold setting unit 124 sets threshold values in histograms of three channels and provides the threshold values to the modeling unit the modeling unit 126, in operation s208.

The modeling unit 126 separates a skin color area except areas such as an eye, lip, naris, beard and the like having information other than the skin color, models the skin color area and binarizes the modeled skin color area using the threshold values, in operation s210.

Subsequently, the signal calculator 130 calculates a mean value of the R, G, B signals for the binarized modeled area and stores the calculated mean value in the buffer 135, in operation s212.

Next, the signal calculator 130 determines whether a predetermined time period, e.g., 30 seconds lapse, in operation s214.

As a result of the determination in the operation s214, when it is determined that the predetermined time period does not lapse, the method returns to the operation s200 for the continuation of the operations as stated above. To put it another way, the signal calculator 130 calculates the mean value of the R, G, B signals in the skin color area only in the face area separated in the input image to store the calculated mean value to the buffer 135.

As a result of the determination in the operation s214, however, when it is determined that the predetermined time period lapse, the signal processor 140 performs a filtering on the R, G, B signals stored accumulatively in the buffer 135 to produce the separated sources 1, 2, 3, in operation s216.

Thereafter, the disguised face discriminator 150 analyzes the frequency features from the separated sources 1, 2, 3 to evaluate the periodicities, in operation s218, and determines whether the separated sources 1, 2, 3 have the pulse component in accordance with the evaluated periodicities, in operation s220.

As a result of the determination in operation s220, when it is determined that there exists the pulse component, the disguised face discriminator 150 discriminates that the face in the input image is genuine, in operation s222; otherwise, the disguised face discriminator 150 discriminates that the face in the input image is a disguised face, in operation s224.

While the invention has been shown and described with respect to the exemplary embodiments, the present invention is not limited thereto. It will be understood by those skilled in the art that various changes and modifications may be made without departing from the scope of the invention as defined in the following claims.

What is claimed is:

1. An apparatus for discriminating a disguised face, the apparatus comprising:
   a face area detector configured to detect a face area in an input image provided from an external source;
   a skin color modeling module configured to separate a skin color area from the face area; and
   a disguised face discriminator configured to determine whether signals in the skin color area have a pulse component to discriminate whether a face in the input image is the disguised face.

2. The apparatus of claim 1, wherein the skin color modeling module comprises:
   a conversion unit configured to perform a coordinate system conversion on an image corresponding to the face area;
   a threshold setting unit configured to set threshold values using the image having the converted coordinate system; and a modeling unit configured to detect the skin color area using the threshold values.

3. The apparatus of claim 2, wherein the modeling unit is configured to perform a binarization on the detected skin color area.

4. The apparatus of claim 3, further comprising:
a signal calculator configured to calculate a mean value of R, G, B signals in the binarized skin color area; and
a buffer configured to store the mean value accumulatively;
wherein the disguised face discriminator is configured to determine whether there exists the pulse component using the mean values stored in the buffer for a predetermined time period.

5. The apparatus of claim 4, wherein the predetermined time period is 3 to 30 seconds.

6. The apparatus of claim 4, further comprising:
a signal processor configured to filter the mean values of the R, G, B signals stored accumulatively in the buffer to produce separated sources 1, 2, 3;
wherein the disguised face discriminator is configured to analyze frequency properties of the separated sources 1, 2, 3 to evaluate periodicities and determine whether there exists the pulse component in accordance with the periodicities.

7. The apparatus of claim 6, wherein the disguised face discriminator is configured to extract the frequency properties by applying FFT, MFCC (Mel-scale Frequency Cepstral Coefficient) and pitch to the separated sources 1, 2, 3 and train the extracted features using an SVM (Support Vector Machine) neural network training machine to determine the presence of the pulse component.

8. The apparatus of claim 2, wherein the conversion unit is configured to convert an RGB image corresponding to the face area into HSV image or YIQ image.

9. The apparatus of claim 2, wherein the RGB image corresponding to the face area is converted into HSV image,
wherein the threshold setting unit is configured to calculate histograms with respect to H, S, V channels of the HSV image and set positions at which a total of pixel counts accumulated in left and right sides about peak positions of the respective histograms becomes a predetermined value to the threshold values for the respective H, S, V channels.

10. A method for discriminating a disguised face, the method comprising:
detecting a face area in an input image provided from an external source;
detecting a skin color area from the face area;
determining whether signals in the skin color area have a pulse component; and
discriminating whether a face in the input image is the disguised face in accordance with the presence of the pulse component.

11. The method of claim 10, wherein said detecting a skin color area comprises:
performing a coordinate system conversion on an image corresponding to the face area;
setting threshold values using the image having the converted coordinate system; and
detecting the skin color area using the threshold values.

12. The method of claim 11, further comprising: performing
a binarization on the detected skin color area.

13. The method of claim 12, further comprising:
calculating a mean value of R, G, B signals in the binarized skin color area; and
accumulatively storing the calculated mean value in a buffer;
wherein said determining whether signals in the skin color area have a pulse component comprises:
determining whether there exists the pulse component using the mean values stored accumulatively in the buffer for a predetermined time period.

14. The method of claim 13, wherein the predetermined time period is 3 to 30 seconds.

15. The method of claim 14, further comprising:
filtering the mean values of the R, G, B signals stored accumulatively in the buffer to produce separated sources 1, 2, 3;
wherein said determining whether signals in the skin color area have a pulse component comprises:
analyzing frequency properties of the separated sources 1, 2, 3 to evaluate periodicities and determine whether there exists the pulse component in accordance with the periodicity.

16. The method of claim 11, wherein said performing a coordinate system conversion comprises:
converting an RGB image corresponding to the face area into an HSV image or YIQ image from which brightness is separated.

17. The method of claim 16, wherein the RGB image corresponding to the face area is converted into an HSV image,
wherein said setting threshold values comprises:
calculating histograms for HSV channels of the HSV image; and
setting the threshold values in the histograms.

18. The method of claim 17, wherein said setting the threshold values in the histograms comprises:
setting positions at which a total of pixel counts accumulated in left and right sides about peak positions of the respective histograms becomes a predetermined value to the threshold values for the respective H, S, V channels.

* * * * *